(12) United States Patent
Essig et al.

(10) Patent No.: US 9,547,010 B2
(45) Date of Patent: Jan. 17, 2017

(54) ANTI-IDIOTYPE ANTIBODY AGAINST AN ANTIBODY AGAINST THE AMYLOID β PEPTIDE

(71) Applicant: Hoffmann-La Roche Inc., Nutley, NJ (US)

(72) Inventors: Ulrich Essig, Planegg (DE); Wolfgang Hoesel, Tutzing (DE); Kay-Gunnar Stubenrauch, Penzberg (DE); Rudolf Vogel, Weilheim (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 211 days.

(21) Appl. No.: 13/960,893

(22) Filed: Aug. 7, 2013

(65) Prior Publication Data

US 2013/0323762 A1 Dec. 5, 2013

Related U.S. Application Data

(62) Division of application No. 12/637,833, filed on Dec. 15, 2009, now Pat. No. 8,614,297.

(30) Foreign Application Priority Data

Dec. 22, 2008 (EP) .................................. 08022235

(51) Int. Cl.
*G01N 33/532* (2006.01)
*C07K 16/42* (2006.01)
*G01N 33/68* (2006.01)

(52) U.S. Cl.
CPC ......... *G01N 33/686* (2013.01); *C07K 16/4241* (2013.01); *C07K 2317/56* (2013.01); *C07K 2317/565* (2013.01); *G01N 2333/4709* (2013.01); *G01N 2469/20* (2013.01)

(58) Field of Classification Search
CPC ........................ C07K 16/4241; C07K 16/4208
See application file for complete search history.

(56) References Cited

U.S. PATENT DOCUMENTS

2005/0169925 A1* 8/2005 Bardroff et al. ........... 424/146.1

FOREIGN PATENT DOCUMENTS

| WO | WO 9006515 A1 * | 6/1990 |
| WO | 2007/101661 | 9/2007 |
| WO | 2008/061684 | 5/2008 |

OTHER PUBLICATIONS

Alberts, Bruce et al. (Ed). Molecular Biology of the Cell, Third Edition. Garland Publishing, New York, 1994, pp. 1216-1220.*
Kuby, Janet (Ed). Immunology, Third Edition. W.H. Freeman & Co. New York, 1997, pp. 131-134.*
Pan Y et al. (1995) Anti-idiotypic antibodies: biological function and structural studies. FASEB J. 9:43-49.*

(Continued)

*Primary Examiner* — Kimberly A. Ballard

(57) ABSTRACT

The present invention is directed to an anti-idiotype antibody binding to the complementary determining region of an antibody against the amyloid β peptide. In one embodiment said antibody binds to the same epitope or an overlapping epitope as the antibody obtainable from the cell line DSM ACC2939. Also reported is an immunoassay for the determination of an antibody against the amyloid β peptide and for determination of an anti-idiotype antibody binding to an antibody against the amyloid β peptide.

4 Claims, 6 Drawing Sheets

(56) References Cited

OTHER PUBLICATIONS

The English translation of the Japanese Office Action, issued on Jun. 17, 2014, in the corresponding Japanese application No. 2011-542710.
The English language translation of the the Korean Office Action, issued on Feb. 10, 2015, in the corresponding Korean Application No. 2013-7019063.

* cited by examiner

SEQUENCE LISTING

<160> NUMBER OF SEQ ID NOS: 13

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Thr His Tyr Ala Arg Tyr Tyr Arg Tyr Phe Asp Val
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Lys Gly Asn Thr His Lys Pro Tyr Gly Tyr Val Arg Tyr Phe Asp
1               5                   10                  15

Val

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Leu Ser Arg Gly Tyr Asn Gly Tyr Tyr His Lys Phe Asp Val
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln Val Tyr Asn Pro Pro Val
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Gln Leu Tyr Ser Asp Pro Phe
1               5

<210> SEQ ID NO 6
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Gln Gln Leu Ser Ser Phe Pro Pro
1               5

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Thr His Tyr Ala Arg Tyr Tyr Arg Tyr Phe Asp Val Trp
            100                 105                 110

Gly Gln Gly Thr Leu Val Thr Val Ser Ser
        115                 120

<210> SEQ ID NO 8
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser
        115                 120                 125
```

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ser Arg Gly Tyr Asn Gly Tyr Tyr His Lys Phe Asp
            100                 105                 110

Val Trp Gly Gln Gly Thr Leu Val Thr Val Ser Ser
        115                 120

<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Val Tyr Asn Pro Pro
                85                  90                  95

Val Thr Phe Gly Gln Gly Thr Lys Val Glu Ile Lys Arg Thr
            100                 105                 110

<210> SEQ ID NO 11
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Leu Thr Gln Ser Pro Ala Thr Leu Ser Leu Ser Pro Gly

```
1               5                   10                  15
Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Phe Gln Leu Tyr Ser Asp Pro
                85                  90                  95

Phe Thr Phe Gly Gln Gly Thr Lys Val Glu Ile Lys Arg Thr
                100                 105                 110
```

<210> SEQ ID NO 12
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Leu Ser Ser Phe Pro
                85                  90                  95

Pro Thr Phe Gly Gln Gly Thr Lys Val Glu Ile Lys Arg Thr
                100                 105                 110
```

<210> SEQ ID NO 13
<211> LENGTH: 42
<212> TYPE: PRT
<213> ORGANISM: Homo sapiens

<400> SEQUENCE: 13

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```

ANTI-IDIOTYPE ANTIBODY AGAINST AN ANTIBODY AGAINST THE AMYLOID β PEPTIDE

PRIORITY TO RELATED APPLICATION(S)

This application is a division of U.S. application Ser. No. 12/637,833, filed Dec. 15, 2009 which claims the benefit of European Patent Application No. 08022235.9, filed Dec. 22, 2008, which is hereby incorporated by reference in its entirety.

The current invention is directed to an anti-idiotype antibody binding to an anti-Aβ antibody and an assay for detecting antibodies binding to the same or an overlapping epitope on an anti-Aβ antibody.

BACKGROUND OF THE INVENTION

About 70% of all cases of dementia are due to Alzheimer's disease which is associated with the selective damage of brain regions and neural circuits critical for cognition. Alzheimer's disease is characterized by neurofibrillary tangles in particular in pyramidal neurons of the hippocampus and numerous amyloid plaques containing mostly a dense core of amyloid deposits and defused halos.

The extracellular neuritic plaques contain large amounts of a pre-dominantly fibrillar peptide termed "amyloid β", "A-beta", "Aβ4", "β-A4" or "Aβ" (see e.g. Selkoe, D. J., Ann. Rev. Cell Biol. 10 (1994) 373-403; Koo, E. H., Proc. Natl. Acad. Sci. USA 96 (1999) 9989-9990; U.S. Pat. No. 4,666,829; or Glenner, G. G., Biochem. Biophysic. Res. Commun. 122 (1984) 1131-1135). This amyloid β peptide is derived from "Alzheimer precursor protein/β-amyloid precursor protein" (APP). APPs are integral membrane glycoproteins (see e.g. Sisodia, S. S., Proc. Natl. Acad. Sci. USA 89 (1992) 6075-6079) and are endoproteolytically cleaved within the Aβ sequence by a plasma membrane protease, α-secretase (see e.g. Sisodia (1992), loc. cit.). Furthermore, further secretase activity, in particular β-secretase and γ-secretase activity, leads to the extracellular release of amyloid-β (Aβ) comprising either 39 amino acids (Aβ39), 40 amino acids (Aβ40), 42 amino acids (Aβ42) or 43 amino acids (Aβ43) (see e.g. Sinha, S., Proc. Natl. Acad. Sci. USA 96 (1999) 11049-11053; Price, D. L., Science 282 (1998) 1079-1083; WO 00/72880; or Hardy, J., Trends in Neuroscience (1997) 154-159).

It is of note that Aβ has several natural occurring forms, whereby the human forms are referred to as the above mentioned Aβ39, Aβ40, Aβ41, Aβ42 and Aβ43. The most prominent form, Aβ42, has the amino acid sequence (starting from the N-terminus): DAEFRHDSGYEVHHQKLVF-FAEDVGSNKGAIIGLMVGGVVIA (SEQ ID NO: 13). In Aβ41, Aβ40, Aβ39, the C-terminal A, IA and VIA, respectively, are missing. In the Aβ43-form an additional threonine residue is comprised at the C-terminus of the above depicted sequence.

Standard solid-phase immunoassays with antibodies involve the formation of a complex between an antibody adsorbed/immobilized on a solid phase (capture antibody), the antigen, and an antibody to another epitope of the antigen conjugated with an enzyme or detectable label (tracer antibody). In the assay, a sandwich is formed: solid phase/capture antibody/antigen/tracer antibody. In the reaction catalyzed by the sandwich among other things the activity of the antibody-conjugated enzyme is proportional to the antigen concentration in the incubation medium. The standard sandwich method is also called double antigen bridging immunoassay because capture and tracer antibodies bind to different epitopes of the same antigen. Hoesel, W., et al. (J. Immunol. Methods 294 (2004) 101-110) report an anti-EPO double antigen bridging assay wherein a mixture of immobilized rhEPO coupled to amino groups and to carbohydrate groups was used. Immunoassays such as the double antigen bridging ELISA are common assay types in the investigation of an immunogenic answer of a patient to a drug antibody. Mire-Sluis, A. R., et al. (J. Immunol. Methods 289 (2004) 1-16) summarize the recommendations for the design and optimization of immunoassays using detection of host antibodies against biotechnology products. Anti-drug antibody assays are mentioned, for example, in WO 2005/045058 and WO 90/006515. Anti-idiotypic antibody assays are mentioned, for example, in U.S. Pat. No. 5,219,730; WO 87/002778; EP 0 139 389; and EP 0 170 302. Wadhwa, M., et al. (J. Immunol. Methods 278 (2003) 1-17) report strategies for the detection, measurement and characterization of unwanted antibodies induced by therapeutic biologicals. In US 2007/0093415 amyloid specific peptides and uses thereof are reported. A method for producing anti idiotypic antibodies is reported in EP 1 917 854.

SUMMARY OF THE INVENTION

The first aspect of the current invention is an anti-idiotype antibody binding to an antibody against the amyloid β peptide as well as its use in an assay according to the invention. In one embodiment said antibody is characterized in binding to the same or an overlapping epitope as the antibody that is obtained from the deposited cell line DSM ACC2939. Another embodiment is that said antibody is the antibody that is obtained from the deposited cell line DSM ACC2939.

Other aspects of the invention are methods for the immunological determination of an antibody against the amyloid β peptide in a sample using an immunoassay and for the immunological determination of an anti-idiotype antibody against an antibody against the amyloid β peptide in a sample using an immunoassay.

In an embodiment of the method for the immunological determination of an antibody against the amyloid β peptide in a sample the immunoassay comprises a capture antibody, a tracer antibody and a detection antibody, wherein the capture antibody is a biotinylated anti-idiotype antibody against an antibody against the amyloid β peptide conjugated to a solid phase via streptavidin, the tracer antibody is an anti-idiotype antibody against an antibody against the amyloid β peptide conjugated to digoxygenin as detectable label, and the detection antibody is an antibody against digoxygenin conjugated to horseradish peroxidase.

In a further embodiment of the method for the immunological determination of an antibody against the amyloid β peptide in a sample the immunoassay comprises the amyloid peptide conjugated to a solid phase, an anti-idiotype antibody against an antibody against the amyloid β peptide conjugated to digoxygenin as detectable label, and a detection antibody against digoxygenin conjugated to horseradish peroxidase.

In one embodiment the anti-idiotype antibody against an antibody against the amyloid β peptide binds to the same or an overlapping epitope as the antibody obtained from the deposited cell line DSM ACC2939. In another embodiment the anti-idiotype antibody against an antibody against the amyloid β peptide is the antibody obtained from the deposited cell line DSM ACC2939.

In one embodiment of the method for the immunological determination of an anti-idiotype antibody against an antibody against the amyloid β peptide in a sample the immunoassay comprises a capture antibody and a tracer antibody, wherein the capture antibody is an antibody against the amyloid β peptide conjugated to a first part of a binding pair and the tracer antibody is an antibody against the amyloid β peptide conjugated to a detectable label. In one embodiment comprises the immunoassay a detection antibody against digoxygenin conjugated to horseradish peroxidase.

In a further embodiment of the method for the immunological determination of an anti-idiotype antibody against an antibody against the amyloid β peptide in a sample the immunoassay comprises the amyloid β peptide conjugated to a solid phase, an antibody against the amyloid β peptide conjugated to digoxygenin as detectable label, and a detection antibody against digoxygenin conjugated to horseradish peroxidase.

In one embodiment of the method according to the invention the immunoassay comprises a capture antibody and a tracer antibody, wherein the capture antibody is a mixture comprising at least two antibodies that differ in the antibody site at which they are conjugated to the solid phase, and the tracer antibody is a mixture comprising at least two antibodies that differ in the antibody site at which they are conjugated to the detectable label.

In one embodiment the conjugation of the antibody to its conjugation partner is performed by chemically binding via N-terminal and/or ε-amino groups (lysine), ε-amino groups of different lysines, carboxy-, sulfhydryl-, hydroxyl- and/or phenolic functional groups of the amino acid backbone of the drug antibody and/or sugar alcohol groups of the carbohydrate structure of the drug antibody. In another embodiment the capture antibody mixture comprises the antibody conjugated via an amino group and via a carbohydrate structure to its conjugation partner.

In one embodiment the antibody against the amyloid β peptide is the antibody as reported in WO 03/070760. In another embodiment the antibody against the amyloid β peptide comprises a heavy chain CDR3 selected from SEQ ID NO: 1, 2 and 3, and a light chain CDR3 selected from SEQ ID NO: 4, 5 and 6. In a further embodiment comprises the antibody against the amyloid β peptide a heavy chain variable domain selected from SEQ ID NO: 7, 8 and 9 and/or a light chain variable domain selected from SEQ ID NO: 10, 11 and 12.

In a further embodiment the capture antibody mixture and/or the tracer antibody mixture comprise the antibody conjugated via at least two different amino groups to its conjugation partner. Such coupling via different amino groups can be performed by acylation of a part of the ε-amino groups with chemical protecting agents, e.g. by citraconylation, in a first step. In a second step conjugation is performed via the remaining amino groups. Subsequently citraconylation is removed and the antibody is conjugated to the conjugation partner via remaining free amino groups, i.e. the antibody obtained is conjugated to the conjugation partner via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

In one embodiment the capture antibody is conjugated to the solid phase by passive adsorption and therefore is conjugated to the solid phase at at least two different antibody sites. Passive adsorption is, e. g., described by Butler, J. E., in "Solid Phases in Immunoassay" (1996) 205-225 and Diamandis, E. P., and Christopoulos, T. K. (Editors), in "Immunoassays" (1996) Academic Press (San Diego).

In one embodiment the tracer antibody mixture comprises the antibody conjugated via an amino group and via a carbohydrate structure to its conjugation partner.

In another embodiment the ratio of capture antibody to tracer antibody is 1:10 to 50:1 (ratio means molar ratio of the antibody molecules irrespective of the molecular weight of the conjugates, which can be different). In still a further embodiment the ratio of amino conjugated antibody (either tracer or capture antibody) to carbohydrate conjugated antibody (either tracer or capture antibody) in such a mixture is 1:10 to 10:1 (ratio means molar ratio of antibody molecules irrespective of the molecular weight of the conjugates, which can be different).

In one embodiment of the invention, the capture antibody is conjugated (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G, etc. In one embodiment the capture antibody is conjugated to biotin and immobilization is performed via immobilized avidin or streptavidin.

In another embodiment the tracer antibody is conjugated to a detectable label. In one embodiment the tracer antibody is conjugated via digoxygenin and an antibody against digoxygenin to the detectable label. Alternatively the tracer antibody is conjugated to an electrochemiluminescent label, like a ruthenium bispyridyl complex.

DETAILED DESCRIPTION OF THE INVENTION

The term "antibody against the amyloid β peptide" according to the invention denotes an antibody which can be administered to an individual, so that a sample of said individual is suspected to comprise said antibody after administration. Within one assay according to the invention, the capture antibody and the tracer antibody comprise the "same" antibody molecule, e.g. recombinantly produced with the same expression vector and comprising the same amino acid sequence. Antibody against the amyloid β peptide are described, for example, in U.S. Pat. No. 7,256,273, U.S. Pat. No. 7,189,819, U.S. Pat. No. 7,179,892, U.S. Pat. No. 7,195,761, US 2008/0281082, US 2008/0221306, US 2008/0131422, US 2008/0050367, US 2007/0238154, US 2007/0154480, US 2007/0110750, US 2006/0280743, US 2006/0292152, US 2006/0165682, US 2006/0057701, US 2006/0057702, US 2006/0039906, US 2005/0249725, US 2005/0169925, US 2005/0118651, US 2005/0009150, US 2004/0171816, US 2004/0171815, and US 2004/0192898.

"Anti-idiotype antibodies" are antibodies, which are directed against the antigen binding site, i.e. the variable region, of a therapeutic antibody, like the complementary determining region. Such anti-idiotype antibodies may occur during antibody therapy as an immunogenic reaction of a patient (see e.g. Pan, Y., et al., FASEB J. 9 (1995) 43-49). In one embodiment said anti-idiotype antibody against an antibody against the amyloid β peptide is binding to one or more of the CDR of the antibody against the amyloid β peptide.

The first aspect of the current invention is an anti-idiotype antibody binding to an antibody against the amyloid β peptide. An exemplary antibody for this aspect of the invention is the antibody that is obtained from the deposited cell line DSM ACC2939. This antibody and its use in an assay according to the invention are also aspects of the current invention. In one embodiment said anti-idiotype antibody is characterized in binding to the same or an overlapping epitope as the antibody that is obtained from the deposited cell line DSM ACC2939. Two epitopes are overlapping if a signal reduction of 50% or more, in one embodiment of 75% or more, is detected by a surface plasmon resonance (SPR) assay using the immobilized antibody and soluble antigen, or vice versa, with the epitope in question at a concentration of 20-50 nM and the antibody for which the epitope overlap has to be detected at a concentration of 100 nM. Alternatively a method can be used in which epitope overlap of two antibodies binding to the same antigen is determined with the help of a competitive test system. For this purpose, for example with the help of a cell-based enzyme immunoassay (ELISA) employing cells expressing recombinant antigen epitopes, it is tested if the antibody for which the epitope overlap has to be detected competes with the other antibody for the binding to the immobilized antigen. For this purpose, the immobilized antigen is incubated with the antibody in labeled form and an excess of the antibody for which the epitope overlap has to be determined. By detection of the bound labeling there can easily be ascertained the epitope overlap. If a signal reduction of more than 70%, in one embodiment of more than 80%, at the same concentration, or a displacement of more than 80%, in one embodiment of more than 90%, at higher concentrations, in one case with a $10^5$-fold excess of the antibody for which epitope overlap has to be determined, referred to the known antibody is determined then epitope identity or overlap is present and both antibodies bind to the same or an overlapping epitope on the same antigen. The anti-idiotype antibody according to the invention is directed against an antibody specifically binding to the amino acid sequence of the amyloid β peptide, e.g. in one embodiment to the amino acid residues of SEQ ID NO: 13.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Monoclonal antibodies and their constant domains contain as proteins a number of reactive side chains for coupling to a binding partner, such as a surface, a protein, a polymer (e.g. PEG, cellulose or polystyrol), an enzyme, or a member of a binding pair. Chemical reactive groups of antibodies are, for example, amino groups (lysines, alpha-amino groups), thiol groups (cystines, cysteines, and methionines), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pp. 50-100.

One of the most common reactive groups of proteins is the aliphatic s-amine of the amino acid lysine. In general, nearly all antibodies contain abundant lysine. Lysine amines are reasonably good nucleophiles above pH 8.0 ($pK_a$=9.18) and therefore react easily and cleanly with a variety of reagents to form stable bonds. Amine-reactive reagents react primarily with lysines and the a-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of proteins to form amide linkages. The anhydride rings open to create multivalent, metal-chelating arms able to bind tightly to metals in a coordination complex.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on proteins, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio)acetate (SATA), and sulfosuccinimidyl 6-[3-(2-pyridyldithio)propionamido]hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in antibodies are carboxylic acids. Proteins contain carboxylic acid groups at the C-terminal position and within the side chains of aspartic acid and glutamic acid. The relatively low reactivity of carboxylic acids in water usually makes it difficult to use these groups to selectively modify proteins and other biomolecules. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site. A Schiff's base intermediate is formed, which can be reduced to an alkyl amine through the reduction of the intermediate with sodium cyanoborohydride (mild and selective) or sodium borohydride (strong) water-soluble reducing agents.

The term "sample" includes, but is not limited to, any quantity of a substance from a living thing or formerly living thing. Such living things include, but are not limited to, humans, mice, monkeys, rats, rabbits, and other animals. Such substances include, but are not limited to, whole blood, serum, or plasma from an individual, which are the most widely used sources of sample in clinical routine.

The term "solid phase" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component of an assay is distinguished from inert solid surfaces with which the assay may be in contact in that a "solid phase" contains at least one moiety on its surface, which is intended to interact with the capture drug antibody. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

From chromogens (fluorescent or luminescent groups and dyes), enzymes, NMR-active groups, metal particles, or haptens, such as digoxygenin, the detectable label is selected in one embodiment. The detectable label can also be a photoactivatable crosslinking group, e.g. an azido or an azirine group. Metal chelates which can be detected by electrochemoluminescence are also in one embodiment signal-emitting groups, with particular preference being given to ruthenium chelates, e.g. a ruthenium (bispridyl)$_3^{2+}$ chelate. Suitable ruthenium labeling groups are described, for example, in EP 0 580 979, WO 90/05301, WO 90/11511, and WO 92/14138.

The invention provides a method for the immunological determination of an anti-idiotype antibody against an antibody against the amyloid β peptide in a sample using an immunoassay comprising a capture antibody and a tracer antibody. In one embodiment the immunoassay is an antigen bridging immunoassay. In another embodiment the immunoassay comprises a capture antibody and a tracer antibody, wherein the capture antibody is a mixture of the antibody against the amyloid β peptide comprising at least two antibodies that differ in the antibody site at which they are conjugated to the solid phase, and the tracer antibody is a mixture of the antibody against the amyloid β peptide comprising at least two antibodies that differ in the antibody site at which they are conjugated to the detectable label.

Commonly/generally employed assays have limitations with respect to the quantification and/or to the determination of an antibody against the amyloid β peptide in a sample, which result e.g. from changes in the binding of the antibody against the amyloid β peptide to the amyloid β peptide. It has been found that by using an antibody against an antibody against the amyloid β peptide (anti-anti-Aβ antibody antibody) according to the current invention in an immunoassay these limitations can be overcome.

The capture antibody useful in a method according to the invention is conjugated to a solid phase. The conjugation is in one embodiment performed by chemical binding via N-terminal and/or ε-amino groups (lysine), c-amino groups of different lysines, carboxy-, sulfhydryl-, hydroxyl- and/or phenolic functional groups of the amino acid backbone of the antibody and/or sugar alcohol groups of the carbohydrate structure of the antibody. The capture antibody useful in a method according to the invention is in one embodiment a mixture of at least two antibodies conjugated to a solid phase, wherein the at least two antibodies conjugated to a solid phase differ in the site at which they are conjugated to the solid phase. For example, the mixture of at least two antibodies conjugated to a solid phase may comprise an antibody against the amyloid β peptide conjugated via an amino acid of the amino acid backbone of the antibody to the solid phase and an antibody against the amyloid β peptide conjugated via a sugar alcohol group of a carbohydrate structure of the antibody to the solid phase. Also, for example, the mixture of at least two antibodies conjugated to a solid phase may comprise antibodies conjugated to the solid phase via different amino acid residues of their amino acid backbone. The expression "different amino acid residue" denotes either two different kinds of amino acids, such as e.g. lysine and aspartic acid, or tyrosine and glutamic acid, or two amino acid residues of the amino acid backbone differing in their position in the amino acid sequence of the antibody. In the latter case the amino acid can be of the same kind or of different kind. The expressions "differ in the antibody site" and "site" denote a difference either in the kind of site, e.g. amino acid or sugar alcohol group, or in the number of the amino acid of the amino acid backbone, e.g. at which the antibody is conjugated to the solid phase. The same applies vice versa to the tracer antibody useful in a method according to the invention.

In one embodiment of the invention comprises the heavy chain variable domain of the antibody against the amyloid β peptide a CDR3 with an amino acid sequence selected from SEQ ID NO: 1, 2, or 3. In a further embodiment the light chain variable domain of said antibody against the amyloid β peptide comprises a CDR3 with an amino acid sequence selected from SEQ ID NO: 4, 5, or 6. In a further embodiment the antibody against the amyloid β peptide comprises a heavy chain variable domain with an amino acid sequence selected from SEQ ID NO: 7, 8, or 9. In still a further embodiment said antibody against the amyloid β peptide comprises a light chain variable domain with an amino acid sequence selected from SEQ ID NO: 10, 11, or 12.

In one embodiment of the method according to the invention the immunoassay comprises as capture antibody the F(ab')$_2$ fragment of a monoclonal antibody against the amyloid β peptide, which is biotinylated and conjugated via streptavidin to a solid phase, and as tracer antibody a polyclonal antibody against human immunoglobulin G conjugated to horseradish peroxidase.

In another embodiment of the method according to the invention the immunoassay is a double antigen bridging immunoassay.

In a further embodiment of the method according to the invention the immunoassay comprises a capture antibody, a tracer antibody and a detection antibody, wherein the capture antibody is a biotinylated antibody against the amyloid β peptide conjugated to a solid phase via streptavidin, the tracer antibody is an antibody against the amyloid β peptide conjugated to digoxygenin, and the detection antibody is an antibody against digoxygenin conjugated to horseradish peroxidase.

In another embodiment of the method according to the invention the immunoassay comprises a capture antibody, a tracer antibody and a detection antibody, wherein the capture antibody is a biotinylated anti-idiotype antibody against an antibody against the amyloid β peptide conjugated to a solid phase via streptavidin, the tracer antibody is an anti-idiotype antibody against an antibody against the amyloid β peptide conjugated to digoxygenin as detectable label, and the detection antibody is an antibody against digoxygenin conjugated to horseradish peroxidase.

In another embodiment of the method according to the invention the immunoassay comprises the amyloid β peptide conjugated to a solid phase, an anti-idiotype antibody against an antibody against the amyloid β peptide conjugated to digoxygenin as detectable label, and a detection antibody against digoxygenin conjugated to horseradish peroxidase.

The mouse-mouse hybridoma cell line according to the invention, hybridoma cell line MAK<Mab31>M-1.5.74, was deposited under the Budapest Treaty on the international recognition of the deposit of microorganisms for the purposes of patent procedure, with Deutsche Sammlung von Mikroorganismen and Zellkulturen GmbH (DSMZ), Germany, on Jul. 29, 2008 under Accession No. DSM ACC2939.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Example 1

Figure 1:
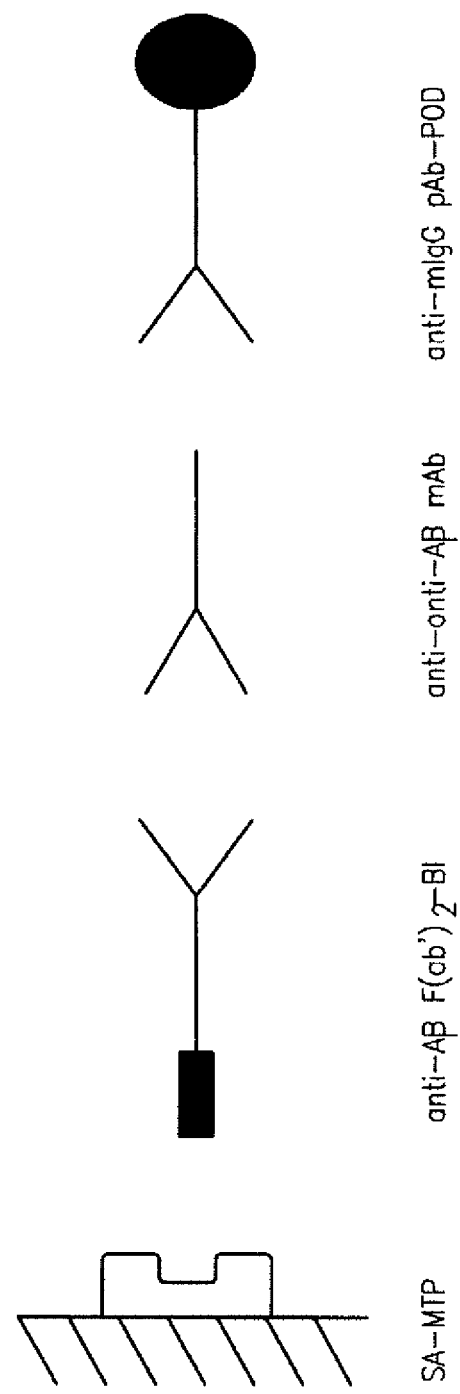
FIG. 1 Selection of anti-idiotype anti-human Aβ antibody antibody.
Figure 2:
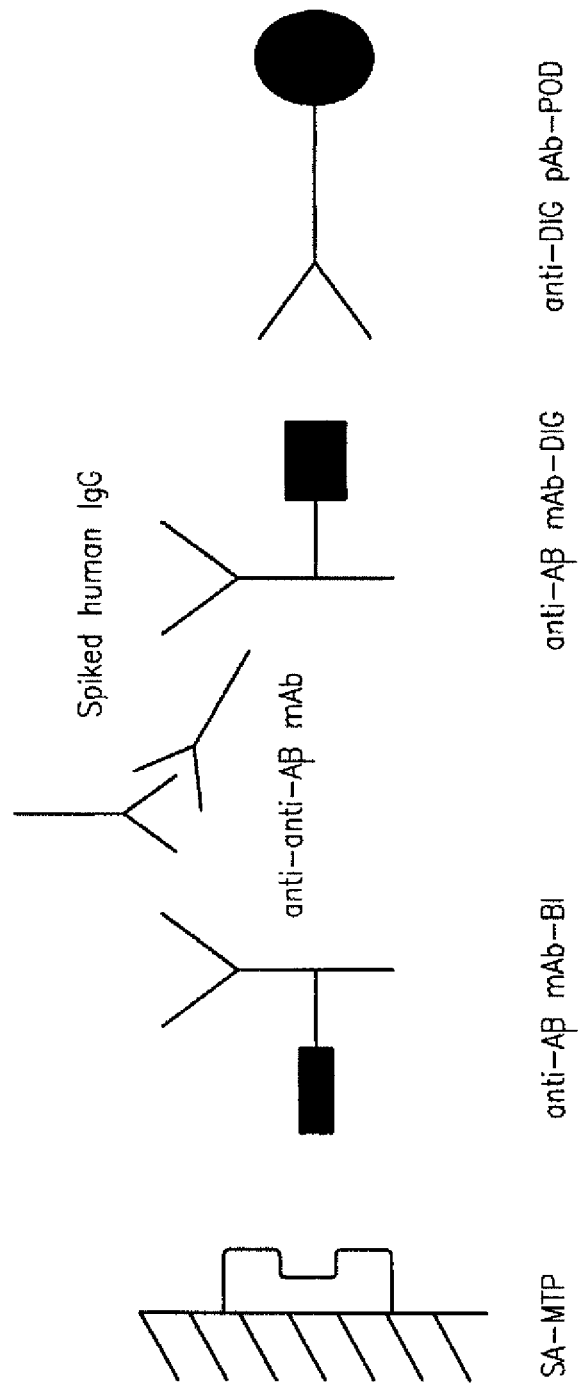
FIG. 2 Assay to evaluate cross-reactivity.
Figure 3:
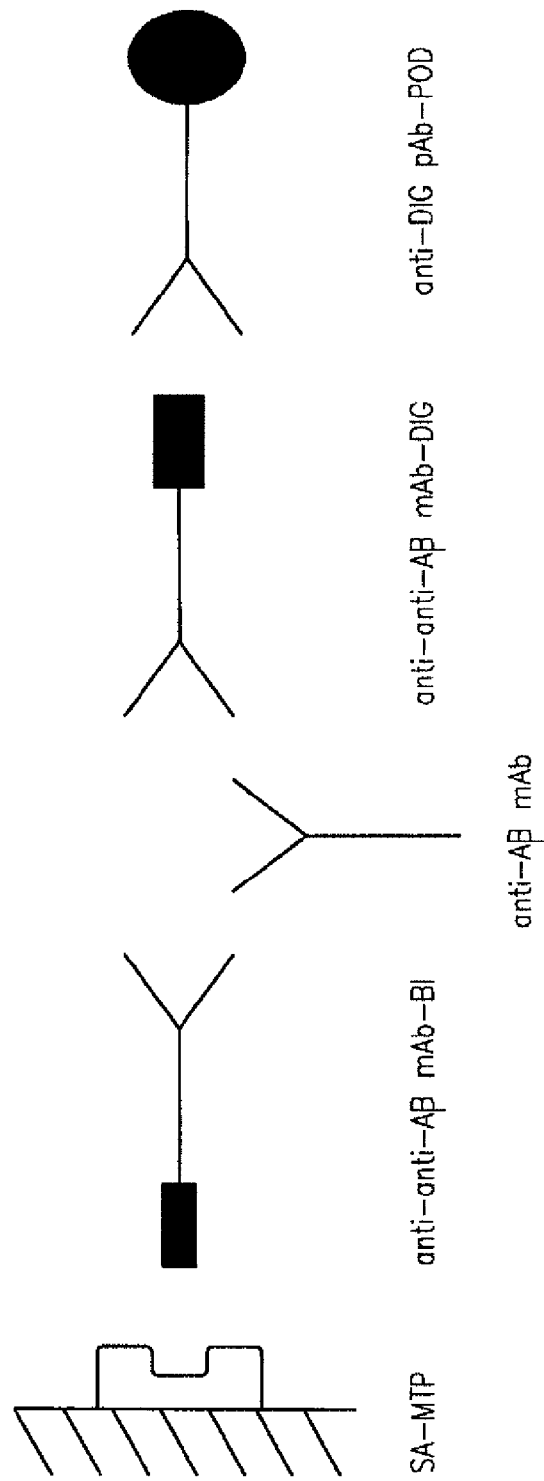
FIG. 3 Quantification of anti-human Aβ antibody.
Figure 4:
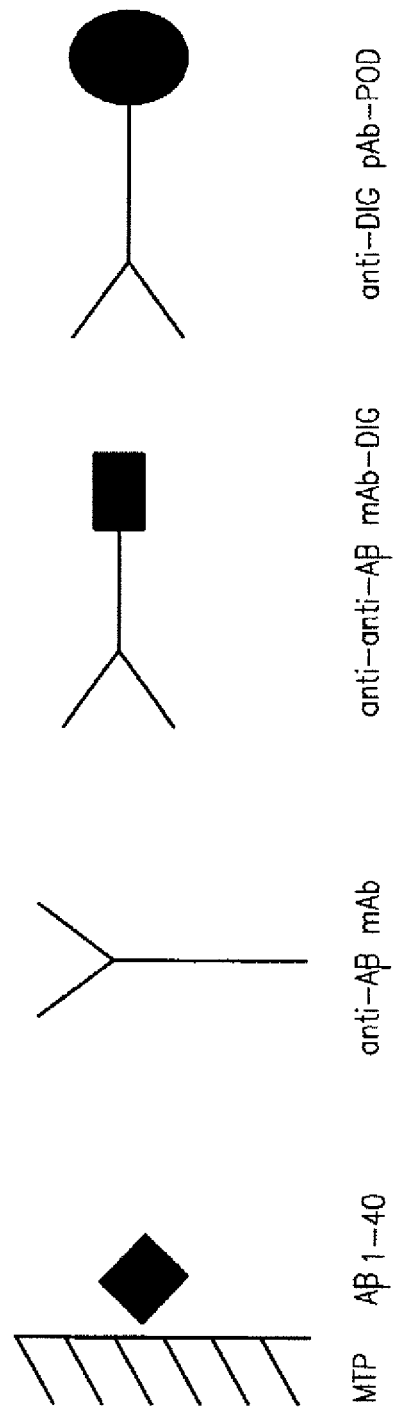
FIG. 4 Alternative assay for quantification of anti-human Aβ antibody.
Figure 5:
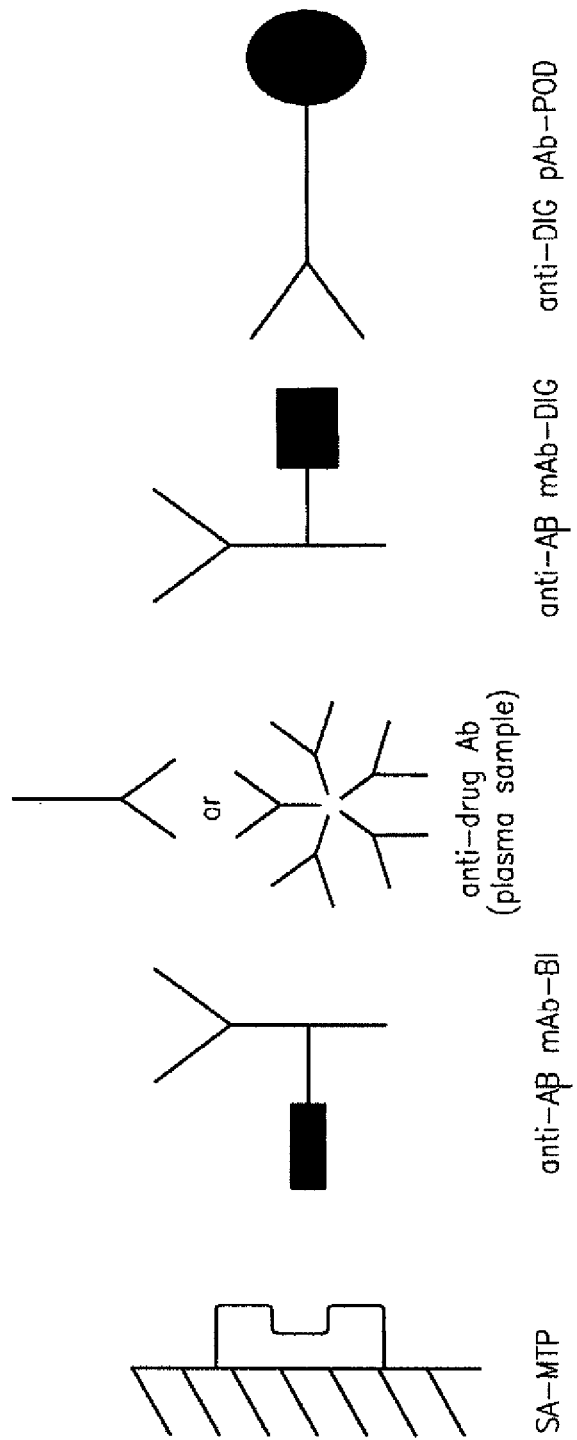
FIG. 5 Detection of anti-anti-human Aβ antibody antibodies (ADA).
Figure 6:
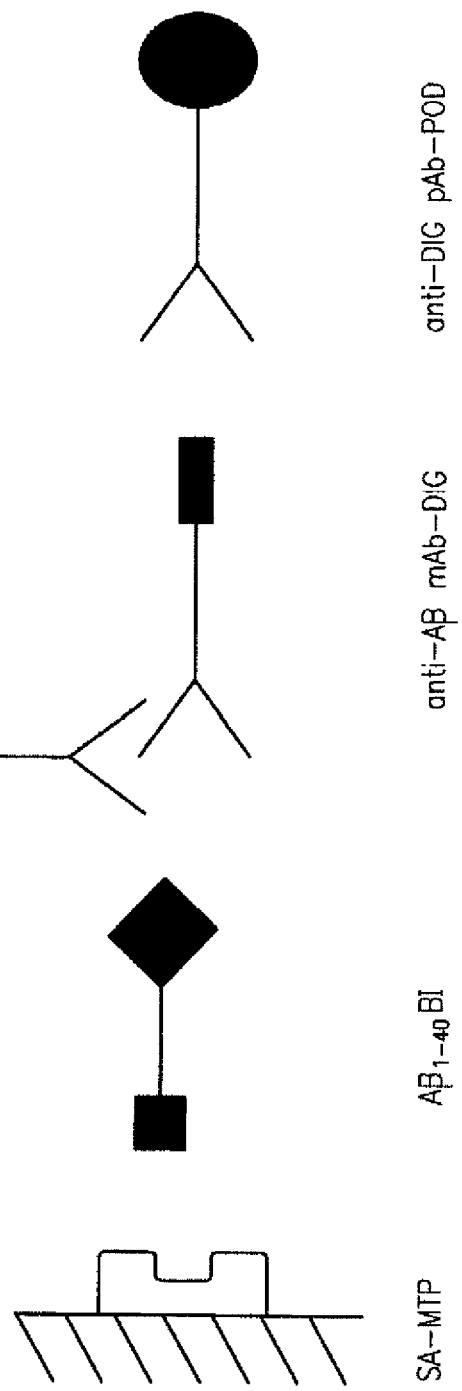
FIG. 6 Detection of neutralizing anti-anti-human Aβ antibody antibodies.

Preparation of the F(ab')$_2$ Fragment of Antibody Against the Amyloid β Peptide For example, an exemplary antibody against the amyloid β peptide (anti-Aβ antibody) and its corresponding nucleic acid sequences are reported in WO 2003/070760 or US 2005/0169925 or in SEQ ID NO: 1 to 12.

The anti-Aβ antibody in 100 mM sodium citrate buffer, pH 3.6, was incubated with pepsin (5 μg pepsin per mg antibody). The fragmentation was analyzed by analytical gel filtration and stopped after 50 minutes by adjusting the pH to 7.0 with potassium phosphate. After dialysis of the mixture against 50 mM potassium phosphate buffer containing 300 mM sodium chloride at pH 7.5 the preparation was concentrated to about 20 mg/ml and applied to a gel filtration column (Superdex 200). The recovered fractions were analyzed by analytical gel filtration and the fractions containing the F(ab')$_2$ fragment were applied to an affinity matrix with immobilized polyclonal antibodies against human Fcγ to eliminate trace amounts of Fcγ containing fragments. The flow through was pooled and finally concentrated to about 20 mg/ml.

Example 2

Generation of Monoclonal Anti-Idiotypic Antibodies a) Immunization of Mice

Female Balb/c or NMRI mice, respectively, 8-12 weeks of age, were primarily immunized intraperitoneally with 100 μg of the F(ab')$_2$ fragment of the monoclonal anti-Aβ antibody comprising a heavy chain variable domain selected from SEQ ID NO: 7 to 9 and a light chain variable domain selected from SEQ ID NO: 10 to 12 mixed with CFA (Complete Freund's Adjuvant) obtained as outlined in Example 1. Three further intraperitoneal immunization steps followed after 4, 7, and 10 weeks, with application of 100 μg of the above-mentioned F(ab')$_2$ fragment per mouse mixed with IFA (Incomplete Freund's Adjuvant). Subsequently, intravenous or intraperitoneal, respectively, boost immunizations were done, each with 25 to 100 μg of F(ab')$_2$ fragment in PBS (phosphate buffered saline) three days before the fusion.

b) Fusion and Cloning

Fusion with myeloma cells derived from the spleen cells of the mice immunized according to a) was performed according to Galfré, G., and Milstein, C. (Galfré, G., and Milstein, C., Methods Enzymol. 73 (1981) 3-46). Approximately 1×10$^8$ splenocytes were mixed with 2×10$^7$ myeloma cells (P3x63-Ag8.653, ATCC CRL1580) and centrifuged (10 min. at 300×g at 4° C.). The cells were washed afterwards once with the culture medium RPMI 1640 without FCS (fetal calf serum), and centrifuged again at 400×g in a 50 ml pointed vial. Thereafter, one ml of PEG (poly (ethylene glycol), molecular weight 4,000 g/mol) was added. Mixing was done by the pipetting. After 1 min. in a water bath at 37° C., 5 ml of RPMI 1640 without FCS were added drop wise. The suspension was mixed, filled up to 50 ml with RPMI 1640 containing 10% (v/v) FCS, and centrifuged afterwards. The sedimented cells were resuspended in RPMI 1640 with 10% FCS, and plated in hypoxanthine-azaserine selection medium (100 mmol/l hypoxanthine, 1 μg/ml azaserine in RPMI 1640 with 10% FCS) containing the growth factor Interleukin 6 (IL-6, 100 U/ml). After approximately 10 days, the primary cultures were assayed for specific antibody synthesis (see Example 3). Primary cultures exhibiting binding to the above-mentioned F(ab')$_2$ fragment as well as no cross reaction with Human IgG, and having been shown to be anti-idiotypic were individualized by single cell deposition into 96-well cell culture plates using a flow cytometer (FACSAria, BD Biosciences), with the medium containing the growth factor Interleukin 6 (100 U/ml). By following this protocol, the deposited clone 1.5.74 was generated (Table 1). The cell line useful in the current invention was deposited with the Deutsche Sammlung von Mikroorganisrnen and Zellkulturen GmbH (DSMZ), Germany.

TABLE 1

Clone producing anti-idiotypic monoclonal antibody

| Clone | IgG Class and Subclass | Deposition No. | Date of deposit |
|---|---|---|---|
| 1.5.74 | IgGX, kappa | DSM ACC2939 | 29 Jul. 2008 | c) Production of Immunoglobulin from the Cell Culture Supernatant

The generated hybridoma cell line was inoculated at an initial cell density of $1.0 \times 10^5$ cells per ml in RPMI 1640 medium supplemented with 10% FCS, and expanded in a spinner culture. From there, a Miniperm unit was inoculated with the cells at an initial cell density (live cells) of $2.4 \times 10^6$ cells per ml in RPMI 1640 medium supplemented with 10% FCS, and expanded. In the harvested culture supernatant, a concentration of 1.2 mg of monoclonal antibody per ml was achieved. Purification of the antibody from the culture supernatant was done according to standard protein chemical methods, e.g. according to Bruck, C., et al., Methods Enzymol. 121 (1986) 587- 596.

Example 3

Screening Assays for Detection of Anti-Idiotypic Antibodies a) Primary Screening for Antibodies Binding to the Drug Antibody For the determination of the specificity of the antibodies in the culture supernatants of the hybridoma cells, MTPs (microtiter plates) pre-coated with recombinant streptavidin (MicroCoat, Bernried, Germany) were coated with biotinylated monoclonal anti-Aβ antibody, 200 ng/ml, or biotinylated human IgG, 2 µg/ml, respectively, in PBS supplemented with 1.0% (w/v) BSA fraction II (100 µl per well, 60 min. incubation at ambient temperature, with shaking). Subsequently the wells were washed three times with 0.9% (w/v) sodium chloride solution containing 0.05% (w/v) Tween® 20. In the next step, per well 100 µl of the antibody solution to be assayed (culture supernatant) were added, and incubated for 60 min. at ambient temperature, with shaking. After three wash steps with 0.9% (w/v) NaCl/0.05% Tween® 20 per well, 100 µl of a horseradish peroxidase-labeled F(ab')$_2$ fragment of a polyclonal sheep anti-mouse Fcγ antibody were added and incubated for 60 min. at ambient temperature, with shaking. Subsequently, washing was performed as above. Finally, per well 100 µl of ABTS® (Roche Diagnostics GmbH, Germany, catalog no. 1684302) were added. After 30 min. incubation at ambient temperature, the extinction (optical density OD) was measured at 405 and 492 nm [405/492] in a commercial microtiter plate ELISA reader. This screening led to a selection of antibodies binding well to monoclonal anti-Aβ antibody IgG as well as exhibiting only a low or even no cross reactivity to human IgG. This selection of antibodies was further subjected to assay b).

b) Selection of Anti-Idiotypic Antibodies

In order to identify, from the selection of antibodies of the primary screening a), those that are anti-idiotypic, the assay described in the following was performed. MTPs pre-coated with recombinant streptavidin (MicroCoat, Bernried, Germany) were coated with biotinylated Aβ peptide, 250 ng/ml, in PBS with 0.5% BSA fraction II (100 µl per well, 60 min. incubation at ambient temperature, with shaking), and subsequently washed three times with 0.9% (w/v) NaCl/0.05% Tween® 20. In the next step, per well 50 µl of the digoxygenin-labeled Fab fragment of monoclonal anti-Aβ antibody, at 2.5-15 ng/ml, and 50 µl of PBS (reference signal), or 50 µl of the candidate antibodies (culture supernatant; assay signal), respectively, were added, and incubated for 60 min. at ambient temperature, with shaking. After three wash steps with 0.9% (w/v) NaCl/0.05% Tween® 20 per well, 100 µl of a horseradish peroxidase-labeled Fab fragment of a polyclonal sheep anti-digoxygenin antibody were added for the detection of bound human monoclonal anti-Aβ antibody-digoxygenin conjugate, and incubated for 60 min, at ambient temperature, with shaking. Subsequently, washing was performed as above. Finally, per well 100 µl of ABTS® (Roche Diagnostics GmbH, Mannheim, Germany, catalog no. 1684302) were added. After 30 min. incubation at ambient temperature, the extinction was measured at [405/492] nm in a commercial microtiter plate ELISA reader. Antibodies exhibiting a strongly reduced assay signal, as compared to the associated reference signal, were selected as candidates for further use.

c) Selection of Antibodies with the Lowest Cross Reactivity to Human IgG

In order to identify, from the candidates of screening b), those that exhibit the lowest cross reactivity to human IgG, the assay described in the following was performed. MTPs pre-coated with recombinant streptavidin (MicroCoat, Bemried, Germany) were coated with biotinylated monoclonal anti-Aβ antibody IgG, 50 ng/ml, in a buffer (125 µl per well, 30 min. incubation at ambient temperature, with shaking), and subsequently washed three times with 0.9% (w/v) NaCl/0.05% Tween® 20. In the next step, per well 100 µl of a mix of 100 µl of the respective candidate antibody (culture supernatant), 100 µl of human IgG (at concentrations up to 73 mg/ml), and 200 µl of digoxygenin-labeled monoclonal anti-Aβ antibody-Fab fragment, were added, and incubated for 60 min. at ambient temperature, with shaking. After three wash steps with 0.9% (w/v) NaCl/0.05% Tween® 20 per well, 100 µl of a horseradish peroxidase-labeled Fab fragment of a polyclonal sheep anti-digoxygenin antibody were added for the detection of bound monoclonal anti-Aβ antibody-Fab-digoxygenin conjugate, and incubated for 60 min. at ambient temperature, with shaking. Subsequently, washing was performed as above. Finally, per well 100 µl of ABTS® (Roche Diagnostics GmbH, Mannheim, Germany, catalog no. 1684302) were added. After 30 min. incubation at ambient temperature, the extinction was measured at [405/492] nm in a commercial microtiter plate ELISA reader. Antibodies exhibiting the least loss of assay signal by the addition of human IgG, as compared to without addition of human IgG, were selected for further use.

Example 4

Purification of Mouse Monoclonal Anti-Idiotypic Antibodies Directed Against Monoclonal Anti-Aβ Antibody The fermentation supernatant of the antibody against monoclonal anti-Aβ antibody IgG was concentrated about tenfold and transferred to a buffer with 20 mM Tris, 1 M ammonium sulfate, pH 9.0, and applied to protein A-sepharose. The eluate with 0.2 M sodium citrate and 0.2 M ammonium sulfate at pH 5.5 was dialyzed against phosphate buffer, pH 7.5. Contaminants of bovine IgG (from FCS in the fermentation broth) were separated by immunoadsorption with immobilized antibodies against bovine IgG.

Example 5

Preparation of Biotinylated Antibody Against Monoclonal Anti-Aβ Antibody

The antibody against monoclonal anti-Aβ antibody-IgG in phosphate buffer, pH 8.5, was adjusted to a protein concentration of about 15 mg/ml. D-biotinoyl-aminocaproic acid-N-hydroxysuccinimide was dissolved in DMSO and added to the solution in a molar ratio of 1:5. The reaction was stopped after 60 minutes by adding L-lysine, and the surplus of the labeling reagent was removed by dialysis against 25 mM potassium phosphate buffer, with 150 mM sodium chloride, pH 7.5, and by gel filtration.

Example 6

Preparation of Digoxigenylated Antibody Against Monoclonal Anti-Aβ Antibody

The antibody against monoclonal anti-Aβ antibody-IgG in phosphate buffer, pH 8.5, was adjusted to a protein concentration of about 15 mg/ml. Digoxygenin 3-O-methylcarbonyl-ε-aminocaproic acid-N-hydroxysuccinimide was dissolved in DMSO and added to the antibody solution in a molar ratio of 1:5. The reaction was stopped after 60 minutes by adding L-lysine, and the surplus of the labeling reagent was removed by dialysis against 25 mM potassium phosphate buffer, with 150 mM sodium chloride, pH 7.5, and by gel filtration.

Example 7

Assay for Quantification of Monoclonal Anti-Aβ Antibody

The ELISA is an assay for the quantitative determination of monoclonal anti-Aβ antibody in human plasma using streptavidin micro titer plates (MTP). The calibration standards and the samples are pre-incubated with a biotinylated and digoxigenylated anti-idiotypic antibody directed against the idiotype of the monoclonal anti-Aβ antibody (-IgG-Bi and -IgG-Dig). After 30 min. pre-incubation the mixture is transferred to the micro titer plate. The Sandwich-ELISA is detected with sheep anti-digoxygenin antibody conjugated to a peroxidase which catalyzes the color reaction of the ABTS® substrate. The signal is determined by an ELISA reader. Washing steps are done before and after incubation with anti-DIG pAb-Fab-POD (pAb=polyclonal antibody). All calibration standards and samples include 10% human plasma.

Example 8

Assay for Detection of an Anti-Drug Antibody Directed Against Monoclonal Anti-Aβ Antibody Biotinylated monoclonal anti-Aβ antibody has been conjugated to (bound onto) the wells of a streptavidin-coated microtiterplate (SA-MTP) in the first step. Not conjugated (unbound) antibody was removed by washing with universal buffer. Afterwards the samples and the reference standards (monoclonal anti-idiotypic anti-Aβ antibody antibody spiked in 5% human serum) have been incubated in the wells. Anti anti-Aβ antibody antibody bound to the immobilized monoclonal anti-Aβ antibody. After having washed away unbound substances the bound anti anti-Aβ antibody antibody was detected with digoxigenylated monoclonal anti-Aβ antibody followed by incubation with a horse-radish peroxidase labeled anti-digoxygenin-antibody (see FIG. 1). The antibody-enzyme conjugate catalyzed the color reaction of the ABTS® substrate. The signal was measured by ELISA reader at 405 nm (reference wavelength: 490 nm). Absorbance values of each serum sample were determined in triplicate.

Example 9

Alternative Assay for Quantification of Monoclonal Anti-Aβ Antibody

The ELISA is an assay for the quantitative determination of monoclonal anti-Aβ antibody in human plasma using micro titer plates (MTP) coated with amyloid beta protein comprising amino acids 1-40 (Aβ(1-40)). The calibrations standards and samples are incubated in the wells of micro titer plates coated with Aβ(1-40) and the amount of monoclonal anti-Aβ antibody bound to Aβ(1-40) coated surface is detected with digoxigenylated anti-idiotypic antibody directed against the idiotype of monoclonal anti-Aβ antibody (-IgG-Dig) and anti-digoxigenin antibody conjugated to peroxidase which catalyzes the color reaction of the ABTS® substrate. The signal is measured by an ELISA reader.

Washing steps are done between all incubation cycles. After coating of the micro titer plate (MTP) with Aβ(1-40) an additional blocking step is necessary (with incubation buffer). All calibration standards and samples include 10% human plasma. All incubation steps are done at room temperature.

Example 10

Assay for Detection of Neutralizing Anti-Drug Antibodies Directed Against Monoclonal Anti-Aβ Antibody For analysis of neutralizing anti-drug antibodies directed against the complementarity-determining region of the monoclonal therapeutic anti-Aβ antibody, a competition ELISA was developed. Plasma samples or anti-idiotypic antibodies against monoclonal anti-Aβ antibody as standard are pre-incubated with monoclonal anti-Aβ antibody-DIG conjugate. Remaining free monoclonal anti-Aβ antibody-DIG conjugate is captured on an Aβ-coated microtiter plate and detected with a peroxidase-labeled anti-digoxygenin antibody and subsequent color reaction with ABTS.

The invention claimed is:

1. A method for the immunological quantification of an anti-amyloid β peptide (anti-Aβ) antibody in a sample, the method comprising the steps of:
providing an immunoassay comprising an antibody obtained from cell line DSM ACC2939, wherein said immunoassay comprises a capture antibody, a tracer antibody and a detection antibody, said tracer antibody is conjugated to a detectable label, wherein at least one of the capture antibody and the tracer antibody is the antibody obtained from cell line DSM ACC2939;
simultaneously or sequentially incubating the capture antibody and the tracer antibody with the sample to form a (capture antibody)-(anti-Aβ antibody)-(tracer antibody) complex;

incubating the (capture antibody)-(anti-Aβantibody)-(tracer antibody) complex with the detection antibody, wherein said detection antibody is directed against the detectable label conjugated to the tracer antibody; and quantifying the amount of said anti-Aβantibody in the sample by determining the presence of the detectable label of the tracer antibody.

2. The method of claim 1, wherein:

said capture antibody is a biotinylated anti-idiotype antibody against an anti-Aβantibody, is obtained from cell line DSM ACC2939, and is conjugated to a solid phase via streptavidin;

said tracer antibody is an anti-idiotype antibody against an anti-Aβantibody, is obtained from cell line DSM AC2939, and is conjugated to digoxygenin as the detectable label; and said detection antibody is directed against digoxygenin and is conjugated to a peroxidase.

3. The method of claim 1, wherein said capture antibody is a mixture comprising at least two of said capture antibodies that differ in the antibody site at which they are conjugated to the solid phase, and the tracer antibody is a mixture comprising at least two of said tracer antibodies that differ in the antibody site at which they are conjugated to the detectable label.

4. A method for the immunological quantification of an anti-amyloid β peptide (anti-Aβ) antibody in a sample, the method comprising the steps of:

providing an immunoassay comprising an anti-idiotype antibody against an anti-Aβ antibody, wherein the anti-idiotype antibody is obtained from cell line DSM ACC2939, and wherein said immunoassay comprises amyloid-βpeptide conjugated to a solid phase, the anti-idiotype antibody obtained from cell line DSM ACC2939 conjugated to digoxygenin as a detectable label, and a peroxidase-conjugated detection antibody directed against digoxygenin;

simultaneously or sequentially incubating the amyloid-βpeptide, the sample and the anti-idiotype antibody together to form a (Aβpeptide)-(anti-Aβantibody)-(anti-idiotype antibody) complex;

incubating the (Aβpeptide)-(anti-Aβantibody)-(anti-idiotype antibody) complex with the detection antibody; and quantifying the amount of said anti-Aβantibody in the sample by determining the presence of the detectable label of the detection antibody.

* * * * *